United States Patent
Tian et al.

(10) Patent No.: US 10,564,103 B2
(45) Date of Patent: Feb. 18, 2020

(54) DUAL-MODE OPTICAL MOLECULAR IMAGING NAVIGATION APPARATUS WITH A SWITCHABLE FIELD OF VIEW AND IMAGING METHOD THEREOF

(71) Applicant: INSTITUTE OF AUTOMATION, CHINESE ACADEMY OF SCIENCES, Beijing (CN)

(72) Inventors: Jie Tian, Beijing (CN); Yamin Mao, Beijing (CN); Chongwei Chi, Beijing (CN); Xin Yang, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 374 days.

(21) Appl. No.: 15/534,882

(22) PCT Filed: Dec. 10, 2014

(86) PCT No.: PCT/CN2014/093474
§ 371 (c)(1),
(2) Date: Oct. 25, 2017

(87) PCT Pub. No.: WO2016/090572
PCT Pub. Date: Jun. 16, 2016

(65) Prior Publication Data
US 2018/0038795 A1  Feb. 8, 2018

(51) Int. Cl.
*A62B 1/04* (2006.01)
*G01N 21/64* (2006.01)
(Continued)

(52) U.S. Cl.
CPC ....... *G01N 21/6456* (2013.01); *G01N 21/251* (2013.01); *G01N 21/359* (2013.01);
(Continued)

(58) Field of Classification Search
USPC .......................................... 348/65
See application file for complete search history.

(56) References Cited

U.S. PATENT DOCUMENTS 8,620,410 B2 * 12/2013 Frangioni ............ A61B 1/0005
600/473
8,977,331 B2 * 3/2015 Kim ..................... A61B 5/0071
382/128
(Continued)

FOREIGN PATENT DOCUMENTS

| CN | 104116497 | 10/2014 |
|---|---|---|
| CN | 104367380 | 2/2015 |
| CN | 204318916 | 5/2015 |

OTHER PUBLICATIONS

International Search Report, issued in the corresponding PCT application No. PCT/CN2014/093474, dated Sep. 9, 2015, 4 pages.

*Primary Examiner* — Nigar Chowdhury
(74) *Attorney, Agent, or Firm* — Hamre, Schumann, Mueller & Larson, P.C.

(57) ABSTRACT

A dual-mode optical molecular imaging navigation apparatus with a switchable field of view, and an imaging method thereof, are provided in the embodiments of the disclosure, the apparatus including: a camera module configured to perform a color imaging and a fluorescence imaging; a switching module configured to switch between an open imaging mode and an endoscopic imaging mode as per imaging requirements; an open imaging module configured to perform observation and imaging with a large field of view; an endoscopic imaging module configured to perform observation and imaging with a deep field of view; a data processing module configured to provide a camera control software and image capturing, processing and display method; and a support module configured to support and connect the navigation apparatus.

8 Claims, 3 Drawing Sheets

(51) Int. Cl.

| | | |
|---|---|---|
| *H04N 5/33* | (2006.01) | |
| *H04N 5/247* | (2006.01) | |
| *H04N 5/232* | (2006.01) | |
| *G01N 21/25* | (2006.01) | |
| *G02B 23/24* | (2006.01) | |
| *G01N 21/359* | (2014.01) | |
| *H04N 5/372* | (2011.01) | |
| *H04N 5/225* | (2006.01) | |
| *G02B 23/26* | (2006.01) | |

(52) U.S. Cl.
CPC ..... *G02B 23/2484* (2013.01); *H04N 5/23296* (2013.01); *H04N 5/247* (2013.01); *H04N 5/332* (2013.01); *H04N 5/372* (2013.01); *G01N 2201/068* (2013.01); *G02B 23/2469* (2013.01); *G02B 23/26* (2013.01); *H04N 2005/2255* (2013.01)

(56) References Cited

U.S. PATENT DOCUMENTS

| | | | |
|---|---|---|---|
| 2006/0030844 A1 | 2/2006 | Knight et al. | |
| 2010/0312122 A1* | 12/2010 | Yazdanfar | A61K 49/0021 600/476 |
| 2011/0117025 A1* | 5/2011 | Dacosta | A61B 5/0059 424/9.6 |
| 2014/0128680 A1* | 5/2014 | Shida | A61B 1/043 600/178 |
| 2018/0276814 A1* | 9/2018 | Frangioni | G06T 7/90 |

* cited by examiner

DUAL-MODE OPTICAL MOLECULAR IMAGING NAVIGATION APPARATUS WITH A SWITCHABLE FIELD OF VIEW AND IMAGING METHOD THEREOF

BACKGROUND OF THE INVENTION

Field of the Invention

Embodiments of the present disclosure relate to the technical field of optical molecular image, and in particular, to an excited fluorescence imaging method, an image processing method, an endoscopic optical molecular imaging navigation method, and an open optical molecular imaging navigation method.

Description of the Related Art

Molecular imaging refers to implement a non-invasive detection and imaging of an organism at the cellular level or the molecular level, e.g., nuclear magnetic resonance (NMR), positron emission tomography (PET), ultrasonic and optical molecular imaging. As an important imaging pattern, optical molecular imaging has been a research hotspot due to its advantages such as low cost, high throughput, non-invasion, non-contact, non-ionizing radiation, high sensitivity, and high specificity. Fluorescence molecular imaging is an important branch of optical molecular imaging, which uses an external light source to excite fluorescence probes within an organism, resulting in a NIR (near-infrared) fluorescence emitted by fluorescence probes. The fluorescence information was detected by a high-sensitivity detector and thus formed fluorescence images.

Nevertheless, the NIR fluorescence light is invisible to naked human eyes and should be observed by a certain apparatus; optical molecular imaging navigation apparatus may assist in learning of the fluorescence information. A traditional navigation apparatus which is in combination with optical molecular image technology is restricted by imaging depth thereof; however, an endoscopic optical molecular imaging navigation system may reach sites deep in an imaging zone, solving a problem of the imaging depth. However, the endoscopic optical molecular imaging navigation system has a relatively small imaging field of view and thus has a limited scope of application.

SUMMARY OF THE INVENTION

The embodiments of the present disclosure have been made to overcome or alleviate at least one aspect of the above mentioned disadvantages and/or shortcomings in the prior art, especially intending to solve problems of imaging depth and imaging width of existing optical molecular imaging navigation systems, a dual-mode optical molecular imaging navigation apparatus with a switchable field of view, and an imaging method thereof, are provided in the disclosure, which may detect a relatively deep imaging zone and may also observe an imaging zone with a relatively large field of view.

According to an aspect of the exemplary embodiment of the present disclosure, there is provided a dual-mode optical molecular imaging navigation apparatus with a switchable field of view, comprising a camera module 10, a switching module 20, an open imaging module 30, an endoscopic imaging module 40, a data processing module 50, and a support module 60; the open imaging module 30 is configured to perform observation and imaging with a large field of view; the endoscopic imaging module 40 is configured to perform observation and imaging with a deep field of view; the switching module 20 is configured to switch between the open imaging module and the endoscopic imaging module selectively, and to establish a connection of an optical signal with the selected imaging module; the camera module 10 is configured to collect and output color and a fluorescence images simultaneously; the data processing module 50 is configured to control the camera module 10, to receive the corresponding color images and fluorescence images outputted from the camera module 10, and to process, store and display the corresponding color images and fluorescence images captured by the camera module 10; and the support module 60 is configured to support and connect other modules, and components thereof.

In an exemplary embodiment of the disclosure, the camera module 10 comprises a color CCD camera 11 configured to be used for the color imaging and a fluorescence CCD camera 12 configured to be used for the fluorescence imaging.

In a further exemplary embodiment of the disclosure, the switching module 20 comprises a light splitting prism 21, a first optical filter 22, a second optical filter 23, a first camera interface 24, a second camera interface 25 and a lens adapter 26; the lens adapter 26 is configured to connect with the open imaging module 30 and the endoscopic imaging module 40 selectively; the light splitting prism 21 is configured to split a light ray transmitted by the lens adapter 26 into two parts so as to feed into the color CCD camera 11 and the fluorescence CCD camera 12 respectively; the first optical filter 22 is configured to filter one of the two divided light rays transmitted from the light splitting prism 21, and to output a light ray having a wavelength ranging between 400 nm~650 nm so as to feed into the color CCD camera 11 through the first camera interface 24; the second optical filter 23 is configured to filter the other of the two divided light rays transmitted from the light splitting prism 21, and to output a light ray having a wavelength ranging between 810 nm~870 nm so as to feed into the fluorescence CCD camera 12 through the second camera interface 25; the first camera interface 24 is configured to transmit the light ray having a wavelength ranging between 400 nm~650 nm which is outputted by the first optical filter 22 into the color CCD camera 11; and the second camera interface 25 is configured to transmit the light ray having a wavelength ranging between 810 nm~870 nm which is outputted by the second optical filter 23 into the fluorescence CCD camera 12.

In a further exemplary embodiment of the disclosure, the open imaging module 30 comprises: an imaging zone 35; a first light source assembly, comprising a first white light source 32, a first NIR (near-infrared) light source 33 and a first optical fiber 34, the first light source assembly being configured to illuminate the imaging zone 35 during use by the first white light source 2 and the first NIR light source 33 through the first optical fiber 34; and a wide-angle lens 31 configured to capture and transmit an optical signal from the imaging zone 35 into the switching module 20.

In a further exemplary embodiment of the disclosure, the endoscopic imaging module 40 comprises: a detected zone 45; a second light source assembly, comprising a second white light source 42, a second NIR (near-infrared) light source 43 and an endoscope optical fiber 44, the second light source assembly being arranged to couple both the second white light source 42 and the second NIR light source 43 directly into the endoscope optical fiber 44 and being configured to feed the endoscope optical fiber 44 into the detected zone 45 so as to capture an optical signal generated by irradiation of the second white light source 42 and the second NIR light source 43 onto the detected zone 45; and an endoscope lens 41 into which the captured light signal is transmitted through the endoscope optical fiber 44 followed by being further transmitted into the switching module 20.

In a further exemplary embodiment of the disclosure, the switching module 20 further comprises a spindle 71 dividing the switching module into a fixed portion which consists of the light splitting prism 21, the first optical filter 22, the second optical filter 23, the first camera interface 24, the second camera interface 25 and the spindle 71, and a rotating portion which connects rotationally with the fixed portion via the spindle 71 and consists of the lens adapter 26 which lens adapter is provided with two throughholes for disposing the open imaging module 30 and the endoscopic imaging module 40 therein respectively and is rotated during use such that an optical axis of the wide-angle lens 31 or the endoscope lens 41 is in line with an optical axis of the fixed portion of the switching module 20.

In a further exemplary embodiment of the disclosure, the data processing module 50 comprises a camera control module 51, an image processing module 52, an image storage module 53, and an image display module 54; the camera control module 51 is configured to adjust parameters of the color CCD camera 11 and the fluorescence CCD camera 12; the image processing module 52 is configured to applying both denoising and pseudo-color adding processing onto the fluorescence images captured by the fluorescence CCD camera 12, and to fuse the color images and the fluorescence images with an image fusion algorithm; the image storage module 53 is configured to store the color images captured by the color CCD camera 11 and the fluorescence images captured by the fluorescence CCD camera 12, as well as the fused images fused by the image processing module 52; and the image display module 54 is configured to display the color images, the fluorescence images and the fused image on a screen in real time.

In a further exemplary embodiment of the disclosure, the support module 60 comprises a camera support 61, a light source support 62, a switching module support 63, a computer support 64, a display support 65, a system support 66; the camera support 61 is configured to support both the color CCD camera 11 and the fluorescence CCD camera 12; the light source support 62 is configured to support the light source; the switching module support 63 is configured to support the switching module 20; the computer support 64 is configured to support a computer; the display support 65 is configured to support a display; and the system support 66 is configured to support and connect other supports within the support module 60.

According to the other aspect of the exemplary embodiment of the present disclosure, there is provided an imaging method of a dual-mode optical molecular imaging navigation apparatus with a switchable field of view, and the method comprises following steps:

Step S1: Selecting one of the open imaging module 30 and the endoscopic imaging module 40 for connecting with the switching module 20 depending on determination by the field of view of a detected zone;

Step S2: Illuminating the detected zone 35 by a first white light source 32 and a first NIR light source 33, adjusting an aperture of a wide-angle lens 31 and focusing the lens, and then capturing simultaneously fluorescence images and color images by a fluorescence CCD camera 12 and a color CCD camera 11 respectively, when the open imaging module 30 is chosen to connect with the switching module 20; or Adjusting an endoscope lens 41 to be focused, increasing both an exposure duration and a gain multiple of the fluorescence CCD camera 12 by a camera control module 51, then turning on a second white light source 42 and a second NIR light source 43, stretching an endoscope optical fiber 44 which communicates optically with the second white light source 42 and the second NIR light source 43 into the detected zone 45, and looking for sites having fluorescence probes by moving the endoscope optical fiber 44 and capturing simultaneously fluorescence images and color images by the fluorescence CCD camera 12 and the color CCD camera 11 respectively, when the endoscopic imaging module 40 is chosen to connect with the switching module 20;

Step S3: Re-implementing Step S1 and Step S2 in a case that the detected zone changes; and Step S4: Fusing the fluorescence images and the color images by an image processing module 52 so as to obtain fused images, and displaying such fused images on a display screen of a computer by an image display module 54.

In an exemplary embodiment of the disclosure, fusing the fluorescence images and the color images comprises following steps:

Step S41: Detecting SIFT feature points within the color images and the fluorescence images;

Step S42: Establishing k-d trees on the color images and the fluorescence images;

Step S43: Matching each of the feature points within the fluorescence images to that of the color images;

Step S44: Calculate a homography matrix H for transformation of the color images into the fluorescence images by choosing four pairs of matched points at random to construct eight systems of linear equations;

Step S45: Calculating consistent sets of H;

Step S46: Obtain a largest consistent set by repeating Step S44 and Step S45 not less than 500 times;

Step S47: Solving H by constructing an overdetermined system of linear equations by all matched points within the largest consistent set at first, and then by adopting a linear least square method;

Step S48: Implementing coordinate transformation, by transforming the color images into a coordinate system of the fluorescence images, by H; and Step S49: Obtaining fused images by implementing pseudo-color adding processing on the fluorescence images and by fusing the fluorescence images after being subjected to pseudo-color adding processing and the color images in one and the same coordinate system.

The disclosure realizes a choice between the open imaging module and the endoscopic imaging module depending on the detected zone, implements a simultaneous capture of both fluorescence images and color images by a light splitter within the switching module, and achieves an effective compatibility between both imaging depth and imaging width which broadens an effective operating range of the molecular imaging navigation system; therefore, it has a wide variety of application scenarios.

BRIEF DESCRIPTION OF THE DRAWINGS

The above and other features and advantages of the present disclosure will become more apparent and a more comprehensive understanding of the present disclosure can be obtained, by describing in detail exemplary embodiments thereof with reference to the accompanying drawings, in which.

DETAILED DESCRIPTION OF PREFERRED EMBODIMENTS OF THE INVENTION

Figure 1:
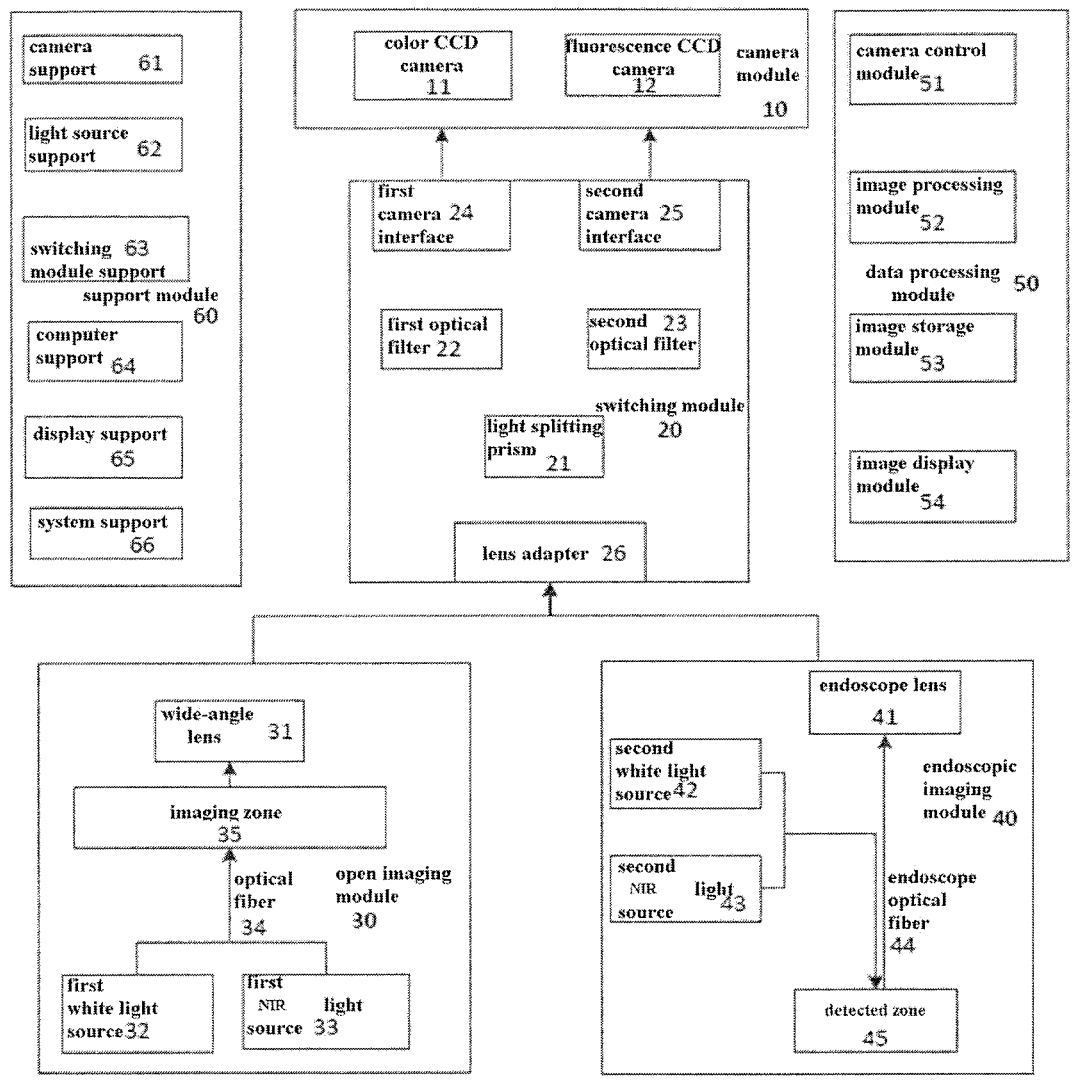
FIG. 1 illustrates a schematic architecture view of a dual-mode optical molecular imaging navigation apparatus with a switchable field of view according to an exemplary embodiment of the disclosure.

Exemplary embodiments of the present disclosure will be described hereinafter in detail with reference to the attached drawings, wherein the like reference numerals refer to the like elements. The present disclosure may, however, be embodied in many different forms, and thus the detailed description of the embodiment of the disclosure in view of attached drawings should not be construed as being limited to the embodiment set forth herein; rather, these embodiments are provided so that the present disclosure will be thorough and complete, and will fully convey the general concept of the disclosure to those skilled in the art.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Respective dimension and shape of each component in the drawings are only intended to exemplarily illustrate the contents of the disclosure, rather than to demonstrate the practical dimension or proportion of components of the dual-mode optical molecular imaging navigation apparatus with a switchable field of view.

According to a general technical concept of embodiments of the present disclosure, as illustrate in FIG. 1, the dual-mode optical molecular imaging navigation apparatus with a switchable field of view, comprises a camera module 10, a switching module 20, an open imaging module 30, an endoscopic imaging module 40, a data processing module 50, and a support module 60.

By way of example, the camera module 10 comprises a color CCD camera 11 configured to be used for the color imaging and a fluorescence CCD camera 12 configured to be used for the fluorescence imaging, so as to take color images and fluorescence images of an optical signal fed into the switching module 20 simultaneously; and the camera module 10 further transmits towards the data processing module 50 corresponding color images and fluorescence images to be inputted there.

Furthermore, by way of example, the switching module 20 comprises a light splitting prism 21, a first optical filter 22, a second optical filter 23, a first camera interface 24, a second camera interface 25 and a lens adapter 26, and is configured to switch between the open imaging module 30 and the endoscopic imaging module 40 selectively and to establish a connection of an optical signal with the selected imaging module. Moreover, by way of example, the light splitting prism 21 is configured to split a light ray transmitted by the lens adapter 26 into two parts so as to feed into the color CCD camera 11 and the fluorescence CCD camera 12 respectively; the first optical filter 22 is configured to filter one of the two divided light rays transmitted from the light splitting prism 21, and to output a light ray having a wavelength ranging between 400 nm~650 nm so as to feed into the color CCD camera 11 through the first camera interface 24; the second optical filter 23 is configured to filter the other of the two divided light rays transmitted from the light splitting prism 21, and to output a light ray having a wavelength ranging between 810 nm~870 nm so as to feed into the fluorescence CCD camera 12 through the second camera interface 25; and the lens adapter 26 is configured to connect with the open imaging module 30 and the endoscopic imaging module 40 selectively.

According to an exemplary embodiment of the disclosure, the switching module is divided into a fixed portion which consists of the light splitting prism 21, the first optical filter 22, the second optical filter 23, the first camera interface 24, the second camera interface 25 and a spindle 71, and a rotating portion which connects rotationally with the fixed portion via the spindle 71 and consists of the lens adapter 26 which lens adapter is provided with two throughholes for disposing the open imaging module 30 and the endoscopic imaging module 40 therein respectively and is rotated during use such that an optical axis of the wide-angle lens 31 or the endoscope lens 41 is in line with an optical axis of the fixed portion of the switching module 20.

By way of example, the open imaging module 30 comprises: a wide-angle lens 31; a first light source assembly, comprising a first white light source 32, a first NIR (near-infrared) light source 33 and a first optical fiber 34; and an imaging zone 35; and the open imaging module 30 is configured to perform observation and imaging with a large field of view. The first light source assembly is configured to illuminate the imaging zone 35 during use by the first white light source 2 and the first NIR light source 33 through the first optical fiber 34; and the wide-angle lens 31 is configured to capture and transmit an optical signal from the imaging zone 35 into the switching module 20.

By way of example, the endoscopic imaging module 40 comprises: an endoscope lens 41; a second light source assembly, comprising a second white light source 42, a second NIR (near-infrared) light source 43 and an endoscope optical fiber 44; and a detected zone 45; and the endoscopic imaging module 40 is configured to perform observation and imaging with a deep field of view. The second light source assembly is arranged to couple both the second white light source 42 and the second NIR light source 43 directly into the endoscope optical fiber 44 and is configured to feed the endoscope optical fiber 44 into the detected zone 45 and to transmit an optical signal thus captured into the endoscope lens 41 through the endoscope optical fiber 44, followed by further transmitting the optical signal into the switching module 20.

By way of example, the data processing module 50 comprises a camera control module 51, an image processing module 52, an image storage module 53, and an image display module 54; and is configured to control the camera module 10 and to process, store and display the corresponding color images and fluorescence images captured by the camera module 10. Furthermore, the camera control module 51 is configured to adjust parameters of the color CCD camera 11 and the fluorescence CCD camera 12; the image processing module 52 is configured to applying both denoising and pseudo-color adding processing onto the fluorescence images captured by the fluorescence CCD camera 12, and to fuse the color images and the fluorescence images with an image fusion algorithm; the image storage module 53 is configured to store the color images captured by the color CCD camera 11 and the fluorescence images captured by the fluorescence CCD camera 12, as well as the fused images fused by the image processing module 52; and the image display module 54 is configured to display the color images, the fluorescence images and the fused image on a screen in real time.

By way of example, the support module 60 comprises a camera support 61, a light source support 62, a switching module support 63, a computer support 64, a display support 65, a system support 66; the camera support 61 is configured to support both the color CCD camera 11 and the fluorescence CCD camera 12; the light source support 62 is configured to support the light source; the switching module support 63 is configured to support the switching module 20; the computer support 64 is configured to support a computer; the display support 65 is configured to support a display; and the system support 66 is configured to support and connect other supports within the support module 60.

In a detailed embodiment of the disclosure, for example, the color CCD camera 11 and the fluorescence CCD camera 12 within the camera module 10 are connected with the switching module 20 through the first camera interface 24 and the second camera interface 25 respectively; the wide-angle lens 31 of the open imaging module 30 or the endoscope lens 41 of the endoscopic imaging module 40 connects with the switching module 20 via the lens adapter 26; the camera control module 51 within the data processing module 50 performs data transmission through a camera data cable with the color CCD camera 11 and the fluorescence CCD camera 12 within the camera module 10; the camera support 61 in the support module 60 is configured to support both the color CCD camera 11 and the fluorescence CCD camera 12; the light source support 62 is configured to support the first white light source 32 and the first NIR light source 33 of open imaging module 30 and the second white light module 42 and the second NIR light source 43 of the endoscopic imaging module 40; the switching module support 63 is configured to support the whole switching module 20; and the computer support 64 is configured to support a computer used in the data processing module 50; and the display support 65 is configured to support a display used in the data processing module 50; and the system support 66 is configured to support various modules and to connect thereamong.

Figure 2:
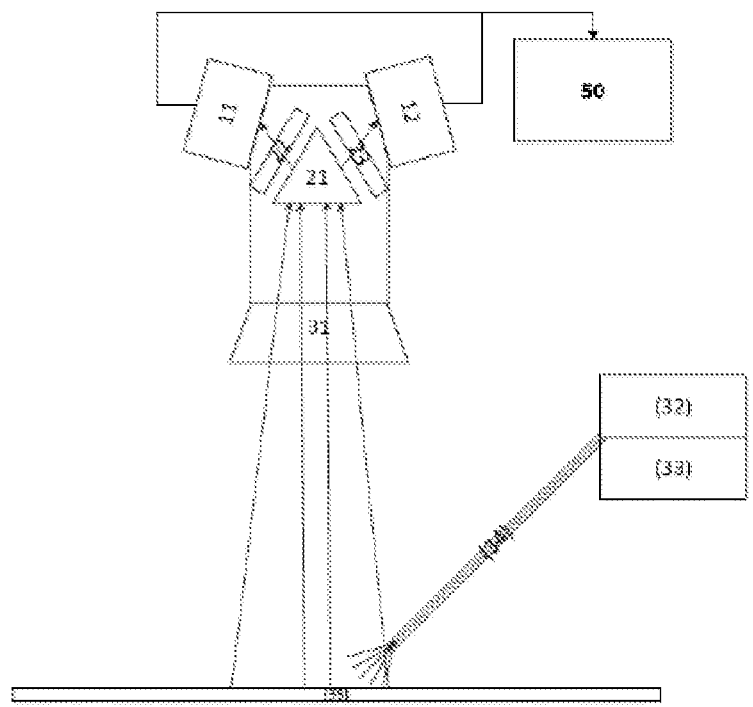
FIG. 2 illustrates a schematic view of an open imaging module of the dual-mode optical molecular imaging navigation apparatus with a switchable field of view according to an exemplary embodiment of the disclosure.

As illustrated in FIG. 2, by way of example, in an embodiment of the disclosure, in an operating condition of the open imaging module, the camera module 10 is used to perform color imaging and fluorescence imaging; the switching module 20 is then connected with the open imaging module 30 so as to divide the optical signal captured by the open imaging module 30 into two parts and to feed into the camera module 10; the open imaging module 30 is then used to provide an open imaging method; and the data processing module 50 is used to provide a camera control software and image capturing, processing and display method.

The open imaging module is provided with an imaging mode as follows: illuminating the imaging zone 35 by the first white light source 32 and the first NIR light source 33; dividing the optical signal captured with the wide-angle lens 31 into two parts, followed by being filtered by the first optical filter 22 and the second optical filter 23 and then being transmitted into the color CCD camera 11 and the fluorescence CCD camera 12 respectively, by the switching module 20; turning on the camera control module 51 within the data processing module 50 so as to open/initiate an image capturing mode, adjusting imaging parameters of the color CCD camera 11 and the fluorescence CCD camera 12, and determining a storage location of images by the image storage module 53; adjusting the aperture of the wide-angle lens 31 so as to change light input (i.e., incoming light) thereof, on the basis of the captured images, and adjusting a lens-focusing button to focus the lens 31; applying denoising, light brightness adjustment and pseudo-color adding processing onto the fluorescence images captured by the fluorescence CCD camera 12, implementing match and fusing processing with the color images, with the image processing module 52, and then displaying the fused images in real time on a computer display screen by the image display module 54 dynamically.

Figure 3:
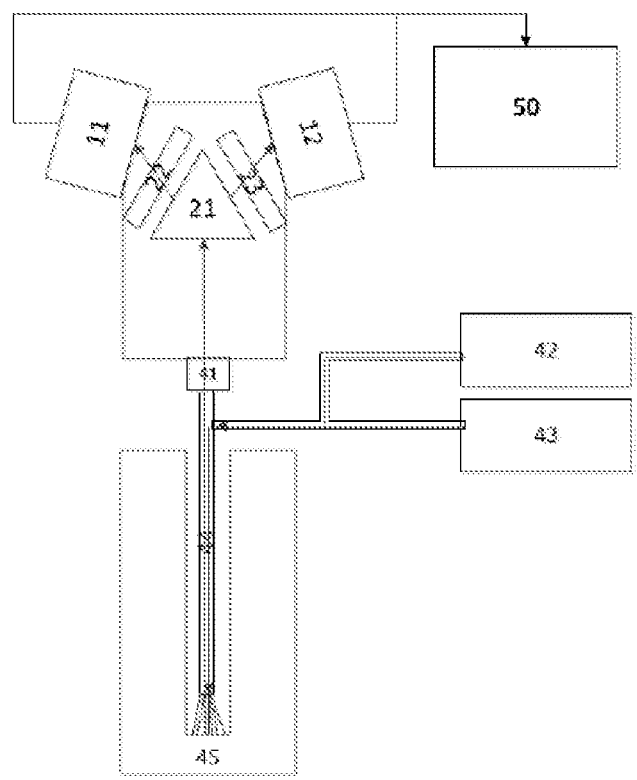
FIG. 3 illustrates a schematic view of an endoscopic imaging module of the dual-mode optical molecular imaging navigation apparatus with a switchable field of view according to an exemplary embodiment of the disclosure.

As illustrated in FIG. 3, by way of example, in an embodiment of the disclosure, in an operating condition of the endoscopic imaging module, the camera module 10 is used to perform color imaging and fluorescence imaging; the switching module 20 is then connected with the endoscopic imaging module 40 so as to divide the optical signal captured by the endoscopic imaging module 40 into two parts and to feed into the camera module 10; the endoscopic imaging module 40 is then used to provide an endoscopic imaging method; and the data processing module 50 is used to provide a camera control software and image capturing, processing and display method.

The endoscopic imaging module is provided with an imaging mode as follows:

connecting the lens adapter 26 of the switching module 20 with the endoscope lens 41 of the endoscopic imaging module 40; connecting the second white light source 42 and the second NIR light source 43 with the endoscope optical fiber 44, and turning on a power switch of the second white light source 42 and the second NIR light source 43; stretching the endoscope optical fiber 44 into the detected zone 45, and dividing the optical signal captured with the endoscope lens 41 into two parts, followed by being filtered by the first optical filter 22 and the second optical filter 23 and then being transmitted into the color CCD camera 11 and the fluorescence CCD camera 12 respectively, by the switching module 20; turning on the camera control module 51 within the data processing module 50 so as to open/initiate an image capturing mode, adjusting imaging parameters of the color CCD camera 11 and the fluorescence CCD camera 12, and determining a storage location of images by the image storage module 53; adjusting the aperture of the endoscope lens 41 so as to change light input (i.e., incoming light) thereof, on the basis of the captured images, and adjusting a lens-focusing button to focus the lens 41; applying denoising, light brightness adjustment and pseudo-color adding processing onto the fluorescence images captured by the fluorescence CCD camera 12, implementing match and fusing processing with the color images, with the image processing module 52, and then displaying the fused images in real time on a computer display screen by the image display module 54 dynamically.

Figure 4:
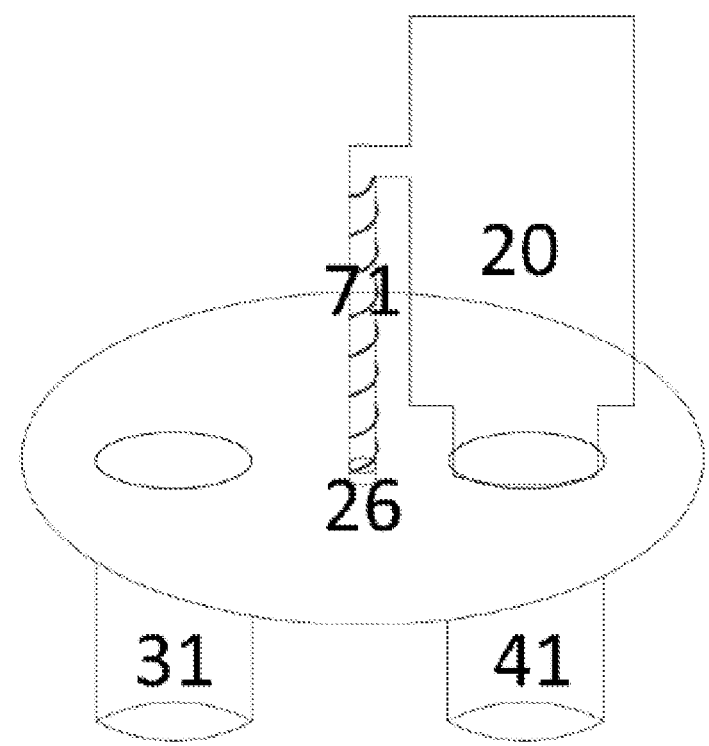
FIG. 4 illustrates a schematic view of transformation of the imaging system of the optical molecular imaging navigation system on the basis of a light splitting prism, according to another exemplary embodiment of the disclosure.

As illustrated in FIG. 4, the lens adapter 26 is connected with the fixed portion of the switching module 20 via the spindle 71, and implements rotational positioning of the lens adapter 26 by a rotational positioning structure and a spring provided on the spindle 71, facilitating switching between the open imaging module 30 and the endoscopic imaging module 40 in the operating condition thereof. In the embodiment of the disclosure, the lens adapter 26 is provided with two throughholes thereon for disposing the open imaging module 30 and the endoscopic imaging module 40 therein respectively and is rotated during use such that an optical axis of the wide-angle lens 31 or the endoscope lens 41 is in line with an optical axis of the fixed portion of the switching module 20.

The imaging method of the exemplary embodiment of the present disclosure comprises following steps:

Step S1: Selecting one of the open imaging module 30 and the endoscopic imaging module 40 for connecting with the switching module 20 by determining a detected zone;

Step S2: Illuminating the detected zone 35 by a first white light source 32 and a first NIR light source 33, adjusting an aperture of a wide-angle lens 31 and focusing the lens, and then capturing fluorescence images and color images by a fluorescence CCD camera 12 and a color CCD camera 11 respectively, when the open imaging module 30 is chosen to connect with the switching module 20; or Adjusting an endoscope lens 41 to be focused, increasing both an exposure duration and a gain multiple of the fluorescence CCD camera 12 by a camera control module 51, then turning on a second white light source 42 and a second NIR light source 43, stretching an endoscope optical fiber 44 which communicates optically with the second white light source 42 and the second NIR light source 43 into the detected zone 45, and looking for sites having fluorescence probes by moving the endoscope optical fiber 44 and capturing simultaneously fluorescence images and color images by the fluorescence CCD camera 12 and the color CCD camera 11 respectively, when the endoscopic imaging module 40 is chosen to connect with the switching module 20;

Step S3: Re-implementing Step S1 and Step S2 in a case that the detected zone changes; and Step S4: Fusing the fluorescence images and the color images by an image processing module 52 so as to obtain fused images, and displaying such fused images on a display screen of a computer by an image display module 54.

In an exemplary embodiment of the disclosure, the method for image fusing processing as adopted in Step S4 comprises following steps:

Step S41: Detecting SIFT feature points within the color images and the fluorescence images;

Step S42: Establishing k-d trees on the color images and the fluorescence images;

Step S43: Matching each of the feature points within the fluorescence images to that of the color images;

Step S44: Calculate a homography matrix H for transformation of the color images into the fluorescence images by choosing four pairs of matched points at random to construct eight systems of linear equations;

Step S45: Calculating consistent sets of H;

Step S46: Obtain a largest consistent set by repeating Step S44 and Step S45 not less than 500 times;

Step S47: Solving H by constructing an overdetermined system of linear equations by all matched points within the largest consistent set at first, and then by adopting a linear least square method;

Step S48: Implementing coordinate transformation, by transforming the color images into a coordinate system of the fluorescence images, by H; and Step S49: Obtaining fused images by implementing pseudo-color adding processing on the fluorescence images and by fusing the fluorescence images after being subjected to pseudo-color adding processing and the color images in one and the same coordinate system.

The disclosure combines advantages of the wide imaging field of view in the open imaging method and the deep imaging field of view in the endoscopic imaging method, and may switch the imaging field of view freely depending on requirements of the imaging field of view by the switching module, so as to realize a choice between the open imaging module and the endoscopic imaging module. And the switching module is of a dual-mode optical structure, therefore it is possible that the light rays captured by the lens (or lenses) are divided into two parts by a light splitter; When the fluorescence images and the color images are captured simultaneously by two CCD cameras respectively, an effective compatibility between both imaging depth and imaging width may be achieved and an effective operating range of the molecular imaging navigation system may also be broadened, by adopting a single apparatus which may choose an appropriate observation mode depending on the detected zone; therefore, it has a wide variety of application scenarios.

During practical use of operators, an appropriate imaging mode may be switched to depending on practical imaging requirements.

It should be appreciated for those skilled in this art that the above embodiments are intended to be illustrated, and not restrictive. For example, many modifications may be made to the above embodiments by those skilled in this art, and various features described in different embodiments may be freely combined with each other without conflicting in configuration or principle.

Although the disclosure is described in view of the attached drawings, the embodiments disclosed in the drawings are only intended to illustrate the preferable embodiment of the present disclosure exemplarily, and should not be deemed as a restriction thereof.

Although several exemplary embodiments of the general concept of the present disclosure have been shown and described, it would be appreciated by those skilled in the art that various changes or modifications may be made in these embodiments without departing from the principles and spirit of the disclosure and lie within the scope of present application, which scope is defined in the claims and their equivalents.

As used herein, an element recited in the singular and proceeded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

What is claimed is:

1. A dual-mode optical molecular imaging navigation apparatus with a switchable field of view, comprising following components:
   an open imaging module configured to perform observation and imaging with a large field of view;
   an endoscopic imaging module configured to perform observation and imaging with a deep field of view;
   switching module configured to switch between the open imaging module and the endoscopic imaging module selectively, and to establish a connection of an optical signal with the selected imaging module;

a camera module configured to perform a color imaging and a fluorescence imaging on the optical signal fed into the switching module simultaneously, and to capture and output corresponding color images and fluorescence images thus generated;

a data processing module configured to control the camera module, to receive the corresponding color images and fluorescence images outputted from the camera module, and to process, store and display the corresponding color images and fluorescence images captured by the camera module; and a support module configured to support and connect other modules, and components thereof, wherein the camera module comprises a color CCD camera configured to be used for the color imaging and a fluorescence CCD camera configured to be used for the fluorescence imaging, and wherein the switching module comprises:

a lens adapter configured to connect with the open imaging module and the endoscopic imaging module selectively;

a light splitting prism configured to divide a light ray transmitted by the lens adapter into two parts so as to feed into the color CCD camera and the fluorescence CCD camera respectively;

a first optical filter configured to filter one of the two divided light rays transmitted from the light splitting prism, and to output a light ray having a wavelength ranging between 400 nm~650 nm;

a second optical filter configured to filter the other of the two divided light rays transmitted from the light splitting prism, and to output a light ray having a wavelength ranging between 810 nm~870 nm;

a first camera interface configured to transmit the light ray having a wavelength ranging between 400 nm~650 nm which is outputted by the first optical filter into the color CCD camera; and a second camera interface configured to transmit the light ray having a wavelength ranging between 810 nm~870 nm which is outputted by the second optical filter into the fluorescence CCD camera.

2. The dual-mode optical molecular imaging navigation apparatus with a switchable field of view according to claim 1, wherein the open imaging module comprises:

an imaging zone;

a first light source assembly, comprising a first white light source, a first NIR light source and a first optical fiber, the first light source assembly being configured to illuminate the imaging zone during use by the first white light source and the first NIR light source through the first optical fiber, and a wide-angle lens configured to capture and transmit an optical signal from the imaging zone into the switching module.

3. A dual-mode optical molecular imaging navigation apparatus with a switchable field of view, comprising following components:

an open imaging module configured to perform observation and imaging with a large field of view;

an endoscopic imaging module configured to perform observation and imaging with a deep field of view;

switching module configured to switch between the open imaging module and the endoscopic imaging module selectively, and to establish a connection of an optical signal with the selected imaging module;

a camera module configured to perform a color imaging and a fluorescence imaging on the optical signal fed into the switching module simultaneously, and to capture and output corresponding color images and fluorescence images thus generated;

a data processing module configured to control the camera module, to receive the corresponding color images and fluorescence images outputted from the camera module, and to process, store and display the corresponding color images and fluorescence images captured by the camera module; and a support module configured to support and connect other modules, and components thereof, wherein the camera module comprises a color CCD camera configured to be used for the color imaging and a fluorescence CCD camera configured to be used for the fluorescence imaging wherein the open imaging module comprises:

an imaging zone;

a first light source assembly, comprising a first white light source, a first NIR light source and a first optical fiber, the first light source assembly being configured to illuminate the imaging zone during use by the first white light source and the first NIR light source through the first optical fiber, and a wide-angle lens configured to capture and transmit an optical signal from the imaging zone into the switching module, and wherein the endoscopic imaging module-comprises:

a detected zone;

a second light source assembly, comprising a second white light source, a second NIR light source and an endoscope optical fiber, the second light source being arranged to couple both the second white light source and the second NIR light source directly into the endoscope optical fiber and being configured to feed the endoscope optical fiber into the detected zone during use so as to capture an optical signal generated by irradiation of the second white light source and the second NIR light source onto the detected zone; and an endoscope lens into which the captured light signal is transmitted through the endoscope optical fiber followed by being further transmitted into the switching module.

4. The dual-mode optical molecular imaging navigation apparatus with a switchable field of view according to claim 3, wherein the switching module further comprises a spindle dividing the switching module into a fixed portion which consists of the light splitting prism, the first optical filter, the second optical filter, the first camera interface, the second camera interface and the spindle, and a rotating portion which connects rotationally with the fixed portion via the spindle and consists of the lens adapter which is provided with two throughholes for disposing the open imaging module and the endoscopic imaging module therein respectively and is rotated during use such that an optical axis of the wide-angle lens or the endoscope lens is in line with an optical axis of the fixed portion of the imaging system switching module.

5. The dual-mode optical molecular imaging navigation apparatus with a switchable field of view according to claim 4, wherein the data processing module comprises:

a camera control module configured to adjust parameters of the color CCD camera and the fluorescence CCD camera;

an image processing module configured to applying both denoising and pseudo-color adding processing onto the fluorescence images captured by the fluorescence CCD camera, and to fuse the color images and the fluorescence images with an image fusion algorithm;

an image storage module configured to store the color images captured by the color CCD camera and the fluorescence images captured by the fluorescence CCD camera, as well as the fused images fused by the image processing module; and an image display module configured to display the color images, the fluorescence images and the fused image on a screen in real time.

6. The dual-mode optical molecular imaging navigation apparatus with a switchable field of view according to claim 5, wherein the support module comprises:

a camera support configured to support both the color CCD camera and the fluorescence CCD camera;

a light source support configured to support the light source;

a switching module support configured to support the switching module;

a computer support configured to support a computer;

a display support configured to support a display; and a system support configured to support and connect other supports within the support module.

7. An imaging method of a dual-mode optical molecular imaging navigation apparatus with a switchable field of view, wherein the method comprises following steps:

Step S1: Selecting one of the open imaging module and the endoscopic imaging module for connecting with the switching module, depending on determination by the field of view of a detected zone;

Step S2: Illuminating the detected zone by a first white light source and a first NIR light source, adjusting an aperture of a wide-angle lens and focusing the lens, and then capturing simultaneously fluorescence images and color images by a fluorescence CCD camera and a color CCD camera respectively, when the open imaging module is chosen to connect with the switching module; or Adjusting an endoscope lens to be focused, increasing both an exposure duration and a gain multiple of the fluorescence CCD camera by a camera control module, then turning on a second white light source and a second NIR light source, stretching an endoscope optical fiber which communicates optically with the second white light source and the second NIR light source into the detected zone, and looking for sites having fluorescence probes by moving the endoscope optical fiber and capturing simultaneously fluorescence images and color images by the fluorescence CCD camera and the color CCD camera respectively, when the endoscopic imaging module is chosen to connect with the switching module;

Step S3: Re-implementing Step S1 and Step S2 in a case that the detected zone changes; and Step S4: Fusing the fluorescence images and the color images by an image processing module so as to obtain fused images, and displaying such fused images on a display screen of a computer by an image display module, wherein the camera module comprises a color CCD camera configured to be used for the color imaging and a fluorescence CCD camera configured to be used for the fluorescence imaging; and wherein the switching module comprises:

a lens adapter configured to connect with the open imaging module and the endoscopic imaging module selectively;

a light splitting prism configured to divide a light ray transmitted by the lens adapter into two parts so as to feed into the color CCD camera and the fluorescence CCD camera respectively;

a first optical filter configured to filter one of the two divided light rays transmitted from the light splitting prism, and to output a light ray having a wavelength ranging between 400 nm~650 nm;

a second optical filter configured to filter the other of the two divided light rays transmitted from the light splitting prism, and to output a light ray having a wavelength ranging between 810 nm~870 nm;

a first camera interface configured to transmit the light ray having a wavelength ranging between 400 nm~650 nm which is outputted by the first optical filter into the color CCD camera; and a second camera interface configured to transmit the light ray having a wavelength ranging between 810 nm~870 nm which is outputted by the second optical filter into the fluorescence CCD camera.

8. The imaging method of a dual-mode optical molecular imaging navigation apparatus with a switchable field of view according to claim 7, wherein fusing the fluorescence images and the color images comprises following steps:

Step S41: Detecting SIFT feature points within the color images and the fluorescence images;

Step S42: Establishing k-d trees on the color images and the fluorescence images;

Step S43: Matching each of the feature points within the fluorescence images to that of the color images;

Step S44: Calculate a homography matrix H for transformation of the color images into the fluorescence images by choosing four pairs of matched points at random to construct eight systems of linear equations;

Step S45: Calculating consistent sets of H;

Step S46: Obtain a largest consistent set by repeating Step S44 and Step S45 not less than 500 times;

Step S47: Solving H by constructing an overdetermined system of linear equations by all matched points within the largest consistent set at first, and then by adopting a linear least square method;

Step S48: Implementing coordinate transformation, by transforming the color images into a coordinate system of the fluorescence images, by H; and Step S49: Obtaining fused images by implementing pseudo-color adding processing on the fluorescence images and by fusing the fluorescence images after being subjected to pseudo-color adding processing and the color images in one and the same coordinate system.

* * * * *